(12) United States Patent
Danford

(10) Patent No.: US 9,579,540 B1
(45) Date of Patent: Feb. 28, 2017

(54) RESISTANCE BREATHING DEVICE

(71) Applicant: TrainingMask L.L.C., Cadillac, MI (US)

(72) Inventor: Casey Danford, Cadillac, MI (US)

(73) Assignee: TrainingMask, L.L.C., Cadillac, MI (US)

( * ) Notice: Subject to any disclaimer, the term of this patent is extended or adjusted under 35 U.S.C. 154(b) by 0 days.

(21) Appl. No.: 14/989,400

(22) Filed: Jan. 6, 2016

(51) Int. Cl.
*A63B 23/18* (2006.01)
*A61M 16/06* (2006.01)
*A61M 16/20* (2006.01)

(52) U.S. Cl.
CPC ......... *A63B 23/18* (2013.01); *A61M 16/0683* (2013.01); *A61M 16/208* (2013.01)

(58) Field of Classification Search
CPC ......... A62B 18/10; A62B 18/02; A62B 18/84; A62B 9/02; A62B 18/025; A62B 18/06; A63B 69/0028; A63B 21/0085; A63B 21/00065; A63B 21/00061; A63B 23/18; A63B 21/00069; A63B 2230/433; A63B 21/0004; A63B 2220/56; A63B 21/0088; A63B 23/025; A63B 21/00058; A63B 21/00076; A63B 21/065; A63B 2213/005; A63B 2213/006; A63B 23/032; A61M 16/0866; A61M 16/0683; A61M 16/208; A61M 16/06; A61M 16/20; A61M 16/201
USPC .......................... 482/10–11, 13; 128/200.24, 128/201.22–201.28, 205.24, 207.12, 128/206.15, 205.25, 206.12–206.19, 128/206.21–207.13
See application file for complete search history.

(56) References Cited

U.S. PATENT DOCUMENTS

| 936,247 A | 10/1909 | Kuhn |
| 3,097,642 A | 7/1963 | Russell |
| 3,633,575 A | 1/1972 | Brumfield |

(Continued)

FOREIGN PATENT DOCUMENTS

| CN | 1311705 A | 9/2001 |
| CN | 3416108 | 12/2004 |

(Continued)

OTHER PUBLICATIONS

Utility U.S. Appl. No. 14/536,794, filed Nov. 10, 2014, entitled "Scent Suppression Mask" (23 pages).

(Continued)

*Primary Examiner* — Andrew S Lo
(74) *Attorney, Agent, or Firm* — Greenberg Traurig, LLP

(57) ABSTRACT

A resistance breathing device includes a face mask having a plurality of apertures extending therethrough. The face mask is adapted to overlay a user's mouth and nose and to form an air-tight seal with the user's face. The device also includes an outer layer overlaying the face mask and having a pair of straps for affixing said face mask about the user's face. The device also includes at least one air admittance valve assembly disposed within a corresponding one of the apertures of the face mask. The air admittance valve assembly is adjustable to provide a selected degree of air flow therethrough. The device also includes at least one air exhaust valve assembly disposed within a corresponding one of the apertures of the face mask. The air exhaust valve assembly prevents air from passing into the face mask and allows air to pass out of the face mask.

17 Claims, 6 Drawing Sheets

(56) References Cited

U.S. PATENT DOCUMENTS

| | | | |
|---|---|---|---|
| 3,850,171 A | 11/1974 | Ball et al. | |
| 4,064,876 A | 12/1977 | Mulchi | |
| 4,221,381 A | 9/1980 | Ericson | |
| 4,549,543 A | 10/1985 | Moon | |
| 4,601,465 A | 7/1986 | Roy | |
| 4,739,987 A | 4/1988 | Nicholson | |
| 4,770,413 A | 9/1988 | Green | |
| 4,961,420 A | 10/1990 | Cappa et al. | |
| 4,973,047 A | 11/1990 | Norell | |
| 5,117,821 A | 6/1992 | White | |
| 5,167,819 A | 12/1992 | Iana et al. | |
| 5,649,533 A * | 7/1997 | Oren | A61M 16/208 128/200.24 |
| 5,697,105 A | 12/1997 | White | |
| 5,799,652 A | 9/1998 | Kotliar | |
| 5,848,589 A | 12/1998 | Welnetz | |
| 5,850,833 A | 12/1998 | Kotliar | |
| 5,924,419 A | 7/1999 | Kotliar | |
| 5,964,222 A | 10/1999 | Kotliar | |
| 6,006,748 A * | 12/1999 | Hollis | A61M 16/208 128/204.18 |
| 6,070,578 A | 6/2000 | Baughman et al. | |
| D440,302 S | 4/2001 | Wolfe | |
| 6,390,094 B1 * | 5/2002 | Slionski | A61M 16/20 128/207.14 |
| 6,471,621 B2 | 10/2002 | Hörstel et al. | |
| 6,508,850 B1 | 1/2003 | Kotliar | |
| 6,554,746 B1 | 4/2003 | McConnell et al. | |
| 6,606,751 B1 | 8/2003 | Kalhok et al. | |
| 6,644,308 B2 | 11/2003 | Kalhok et al. | |
| 6,986,745 B2 * | 1/2006 | Farr | A61B 5/087 600/529 |
| 7,523,755 B2 | 4/2009 | Richardson et al. | |
| 7,931,733 B2 | 4/2011 | Kotliar | |
| D645,956 S | 9/2011 | Grimsley | |
| 8,365,734 B1 | 2/2013 | Lehman | |
| D681,192 S | 4/2013 | D'Souza et al. | |
| 8,443,806 B2 * | 5/2013 | Morelli | 128/207.12 |
| 8,590,533 B2 | 11/2013 | Danford | |
| D694,875 S | 12/2013 | D'Souza et al. | |
| 8,678,005 B2 * | 3/2014 | Dawson | A61M 16/0468 128/205.24 |
| 8,695,599 B2 * | 4/2014 | Friberg | A61M 16/205 128/204.18 |
| 9,067,086 B2 | 6/2015 | Danford | |
| 2001/0007651 A1 | 7/2001 | Fust | |
| 2001/0029750 A1 | 10/2001 | Kotliar | |
| 2002/0023762 A1 | 2/2002 | Kotliar | |
| 2002/0100893 A1 | 8/2002 | Shultz | |
| 2002/0162556 A1 | 11/2002 | Smith et al. | |
| 2003/0005934 A1 | 1/2003 | Japuntich et al. | |
| 2004/0146842 A1 | 7/2004 | Carlucci et al. | |
| 2004/0226563 A1 | 11/2004 | Xu et al. | |
| 2008/0092898 A1 * | 4/2008 | Schneider | A61B 5/0878 128/206.28 |
| 2008/0178884 A1 | 7/2008 | Gerson et al. | |
| 2008/0202774 A1 | 8/2008 | Kotliar | |
| 2008/0210240 A1 | 9/2008 | Kotliar | |
| 2009/0320848 A1 | 12/2009 | Steindorf et al. | |
| 2010/0101584 A1 | 4/2010 | Bledstein et al. | |
| 2011/0212811 A1 | 9/2011 | Rutten | |
| 2012/0094806 A1 * | 4/2012 | Danford | A63B 21/0004 482/13 |
| 2012/0103339 A1 | 5/2012 | Koehler | |
| 2013/0060157 A1 * | 3/2013 | Beard | A61M 16/06 600/532 |
| 2013/0190643 A1 * | 7/2013 | Brambilla | A61M 16/0066 600/543 |
| 2013/0319420 A1 | 12/2013 | Danford | |
| 2014/0251332 A1 * | 9/2014 | Martin | A61M 16/0833 128/203.29 |
| 2015/0040907 A1 * | 2/2015 | Hakim | A61M 16/0683 128/205.24 |
| 2015/0231443 A1 * | 8/2015 | Halliday | A63B 23/18 482/13 |
| 2016/0089553 A1 | 3/2016 | Dickstein et al. | |

FOREIGN PATENT DOCUMENTS

| | | |
|---|---|---|
| CN | 3525464 | 4/2006 |
| CN | 3611368 | 2/2007 |
| CN | 300733965 | 1/2008 |
| CN | 300798841 S | 7/2008 |
| CN | 300853751 S | 11/2008 |
| CN | 301345091 S | 9/2010 |
| CN | 301345092 S | 9/2010 |
| CN | 102421485 A | 4/2012 |
| CN | 302364261 S | 3/2013 |
| CN | 302560932 S | 9/2013 |
| CN | 302675148 S | 12/2013 |
| CN | 203523849 U | 4/2014 |
| CN | 302827495 S | 5/2014 |
| CN | 302857904 S | 6/2014 |
| CN | 302857912 S | 6/2014 |
| CN | 302857913 S | 6/2014 |
| CN | 302919473 S | 8/2014 |
| CN | 302945765 S | 9/2014 |
| CN | 303061361 S | 12/2014 |
| CN | 303312122 S | 7/2015 |
| EP | 2 425 875 A1 | 3/2012 |
| JP | D2004-19667 | 4/2005 |
| JP | 2010-42087 A | 2/2010 |
| JP | D2010-021935 | 7/2011 |
| KR | 30-0514514 | 12/2008 |
| KR | 30-2008-0014298 | 4/2009 |
| KR | 20-2010-0004312 U | 4/2010 |
| KR | 30-0586700 | 1/2011 |
| KR | 30-0778665 | 1/2015 |
| WO | 00/04957 A1 | 2/2000 |
| WO | 2010/127161 A2 | 11/2010 |
| WO | 2010/127161 A3 | 11/2010 |
| WO | DM/082862 | 2/2014 |

OTHER PUBLICATIONS

Utility U.S. Appl. No. 14/535,641, filed Nov. 7, 2014, entitled "Breathing Mask With Variable Airflow Resistance Insert" (28 pages).

Design U.S. Appl. No. 29/544,300, filed Nov. 2, 2015, entitled "Resistance and Filtration Breathing Device" (7 pages).

Design U.S. Appl. No. 29/544,580, filed Nov. 4, 2015, entitled "Resistance Breathing Device" (7 pages).

International Search Report and Written Opinion dated Dec. 7, 2015, issued in International (PCT) Patent Application No. PCT/US2015/051364, filed Sep. 22, 2015 (15 pages).

Utility U.S. Appl. No. 14/951,837, filed Nov. 25, 2015, entitled "Resistance and Filtration Breathing Device" (42 pages).

Office Action for Applicant's related Japan Design Application No. 2016-001555, mailed Jul. 5, 2016 by the Japanese Patent Office, and English-language translation thereof (4 pages).

ReBNA product catalogue published by Patent Works, Inc., obtained by the Japan National Center for Industrial Property Information and Training on Mar. 21, 2008 (1 page).

Design Patent Right Evaluation Report completed Jul. 4, 2016, issued by the State Intellectual Property Office of China in Applicant's related China Design Patent No. ZL201530482604.X and English-language translation thereof (18 pages).

Design Patent Right Evaluation Report completed Jul. 4, 2016, issued by the State Intellectual Property Office of China in Applicant's related China Design Patent No. ZL201530482542.2 and English-language translation thereof (23 pages).

Patentability Assessment Report, completed Jul. 20, 2016, issued by the State Intellectual Property Office of China in Applicant's related China Utility Patent No. ZL2010208912778 (7 pages).

International Search Report and the Written Opinion of the International Searching Authority, mailed Aug. 8, 2016, issued by the

(56) References Cited

OTHER PUBLICATIONS

European Patent Office in Applicant's related International Application No. PCT/US2015/064042 (11 pages).
Design Patent Right Evaluation Report dated Mar. 21, 2016, issued by the State Intellectual Property Office of China in Patent No. ZL201530349470.4 and English-language translation thereof (31 pages).

* cited by examiner

RESISTANCE BREATHING DEVICE

FIELD OF THE INVENTION

The present invention relates to wearable breathing devices. More particularly, the present invention relates to wearable breathing masks providing resistance to air inhalation.

BACKGROUND OF THE INVENTION

Individuals who are training for physical fitness or athletic competition may wish to improve the efficiency of their cardiovascular systems for improved health and stamina. There is a need for devices that provide inhalation resistance to assist in such training.

SUMMARY OF THE INVENTION

In an embodiment, a resistance breathing device includes a face mask having an exterior surface, an interior surface opposite the exterior surface, a plurality of apertures, and a perimeter. Each of the plurality of apertures extends through the face mask from the exterior surface to the interior surface. The face mask is adapted to overlay a user's mouth and nose such that the perimeter forms an air-tight seal with the user's face and around the user's mouth and nose and the face mask defines an internal area between the interior surface of the face mask and the user's face. The resistance breathing device also includes an outer layer overlaying the face mask and having a pair of straps with inter-engaging ends for affixing the face mask about the user's face. The resistance breathing device also includes at least one air admittance valve assembly disposed within a corresponding one of the plurality of apertures of the face mask. The at least one air admittance valve assembly is adjustable to provide a selected degree of air flow therethrough. The resistance breathing device also includes at least one air exhaust valve assembly disposed within a corresponding one of the plurality of apertures of the face mask. The at least one air exhaust valve assembly is adapted to prevent air from passing therethrough from an external environment to the internal area. The at least one air exhaust valve assembly is adapted to allow air to pass therethrough from the internal area to the external environment.

In an embodiment, the at least one air admittance valve assembly includes a cylindrical base having a first end, a second end opposite the first end, a cylindrical body extending from the first end to the second end, and an air passageway extending through the cylindrical body from the first end to the second end. The cylindrical base is disposed within a corresponding one of the plurality of apertures of the face mask such that the first end of the cylindrical base is proximate the interior surface of the face mask and the second end of the cylindrical base is proximate the exterior surface of the face mask. The cylindrical base is sized and shaped such that the corresponding one of the plurality of apertures of the face mask forms an air-tight seal about the cylindrical base. The at least one air admittance valve assembly also includes a cap attached to the second end of the cylindrical base. The cap is movable relative to the cylindrical base to provide the selected degree of air flow.

In an embodiment, the cylindrical base includes an end portion occluding the air passageway of the cylindrical base proximate the second end of the cylindrical base. The end portion includes a first plurality of holes extending therethrough. The first plurality of holes is arranged in arcuate arrangement. The cap includes a second plurality of holes extending therethrough. The second plurality of holes is arranged in arcuate arrangement. The cap is rotatable relative to the cylindrical base to selectively align one or more of the first plurality of holes of the base with a corresponding one or more of the second plurality of holes of the cap. The selective alignment provides the selected degree of air flow.

In an embodiment, the base includes a projection extending from the end portion toward the cap. The cap includes a depression receiving the projection of the base therein. The depression has a first end and a second end opposite the first end. The rotation of the cap relative to the base causes the depression of said the to move relative to the projection of the base such that the first end of the depression of the cap is adjacent the projection of the base when one of the second plurality of holes of the cap is aligned with one of the first plurality of holes of the base, and such that the second end of the depression of the cap is adjacent the projection of the base when each of the second plurality of holes of the cap is aligned with a corresponding one of the first plurality of holes of the base.

In an embodiment, the base includes at least one ridge projecting from the cylindrical body. The cap includes at least one groove formed therein. The at least one ridge of the base and the at least one groove of said cap are positioned such that the at least one ridge is positioned within a corresponding one of the at least one groove when one or more of the second plurality of holes of the cap is aligned with a corresponding one of the first plurality of holes of the base. In an embodiment, when the at least one ridge is positioned within the corresponding at least one groove, the at least one ridge cooperates with the at least one groove to resist rotation of the cap relative to the base.

In an embodiment, the base includes at least one flange sized, shaped and positioned to retain the base within the face mask. In an embodiment, the base and the cap are each made from a plastic material.

In an embodiment, the at least one air exhaust valve assembly includes a cylindrical base having a first end, a second end opposite the first end, and an air passageway extending therethrough from the first end to the second end. The cylindrical base is disposed within a corresponding one of the plurality of apertures of the face mask such that the first end of the cylindrical base is proximate the interior surface of the face mask and the second end of the cylindrical base is proximate the exterior surface of the face mask. The cylindrical base is sized and shaped such that the corresponding one of the plurality of apertures of the face mask forms an air-tight seal about the cylindrical base. The cylindrical base also includes a biasing member extending across the air passageway proximate the first end and a stem extending from a center of the biasing member toward the second end. The at least one air exhaust valve assembly also includes a flexible membrane having a first side, a second side opposite the first side, a profile complementary to the air passageway, a post extending from the first side, and a central hole extending through the post and the flexible membrane. The flexible membrane is disposed within the cylindrical base such that the stem of said cylindrical base is disposed within the central hole of the flexible membrane. The at least one air exhaust valve assembly also includes a cap having a first side and a second side opposite the first side of the cap. The cap is attached to the second end of the cylindrical base. A post extends from the first side of the cap and has a central bore receiving the stem of the base. In an embodiment, in response to an inhalation by the user, the flexible membrane is urged to a position flush against the biasing member of the base, whereby the flexible membrane seals the air passageway of the base. In an embodiment, in response to an exhalation by the user, said flexible membrane is urged away from the biasing member of the base, whereby air can pass freely through the air passageway of the base. In an embodiment, the flexible membrane is made from silicone. In an embodiment, the cap and the base are each made from a plastic material. In an embodiment, the base includes at least one flange sized, shaped and positioned to retain the base within the face mask.

In an embodiment, the resistance breathing device includes a plurality of air admittance valve assemblies. In an embodiment, the resistance breathing device includes a plurality of air exhaust valve assemblies. In an embodiment, the outer layer includes a fabric material. In an embodiment, the fabric material includes an elastic material. In an embodiment, the straps of the outer layer include hook-and-loop fasteners. In an embodiment, the face mask includes rubber.

BRIEF DESCRIPTION OF THE DRAWINGS

Reference is made to the following detailed description of the exemplary embodiment considered in conjunction with the accompanying drawings, in which.

DETAILED DESCRIPTION OF THE EXEMPLARY EMBODIMENTS

Figure 1:
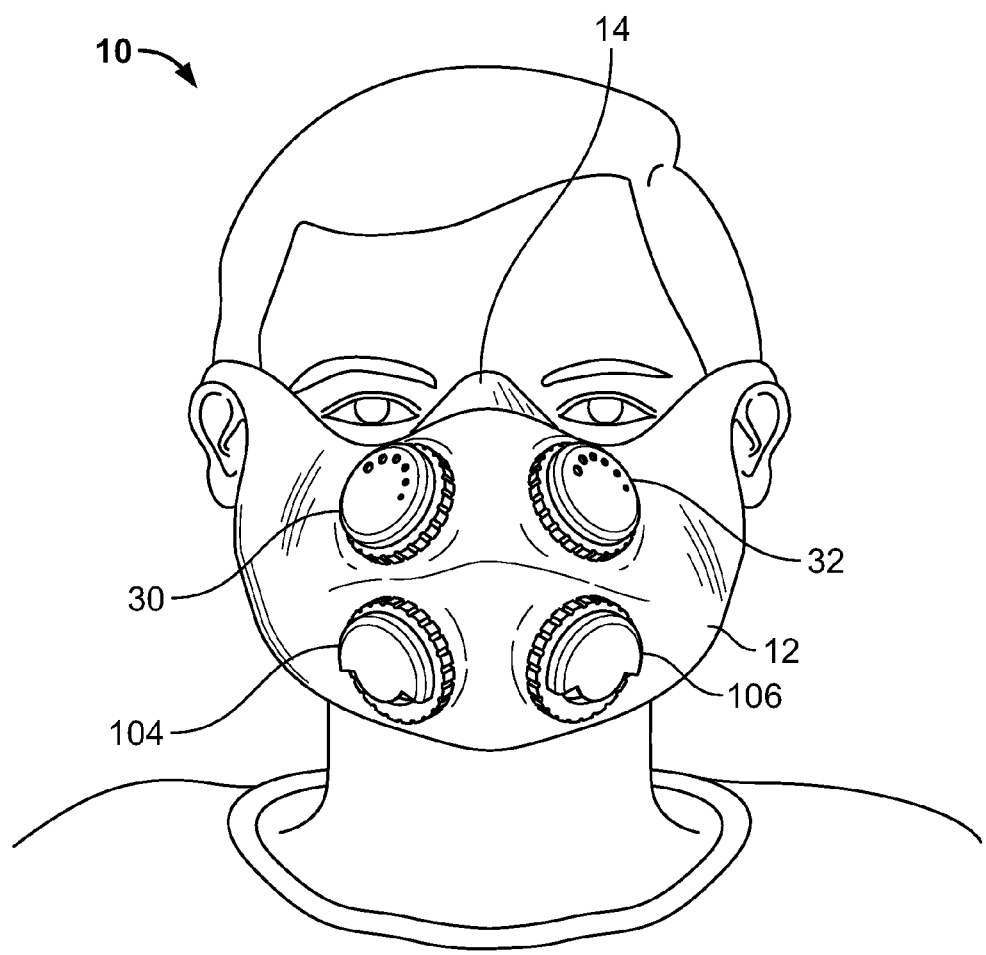
FIG. 1 is a front elevational view of a resistance breathing device in accordance with a first exemplary embodiment of the present invention, said device being shown as worn by a user.
Figure 2:
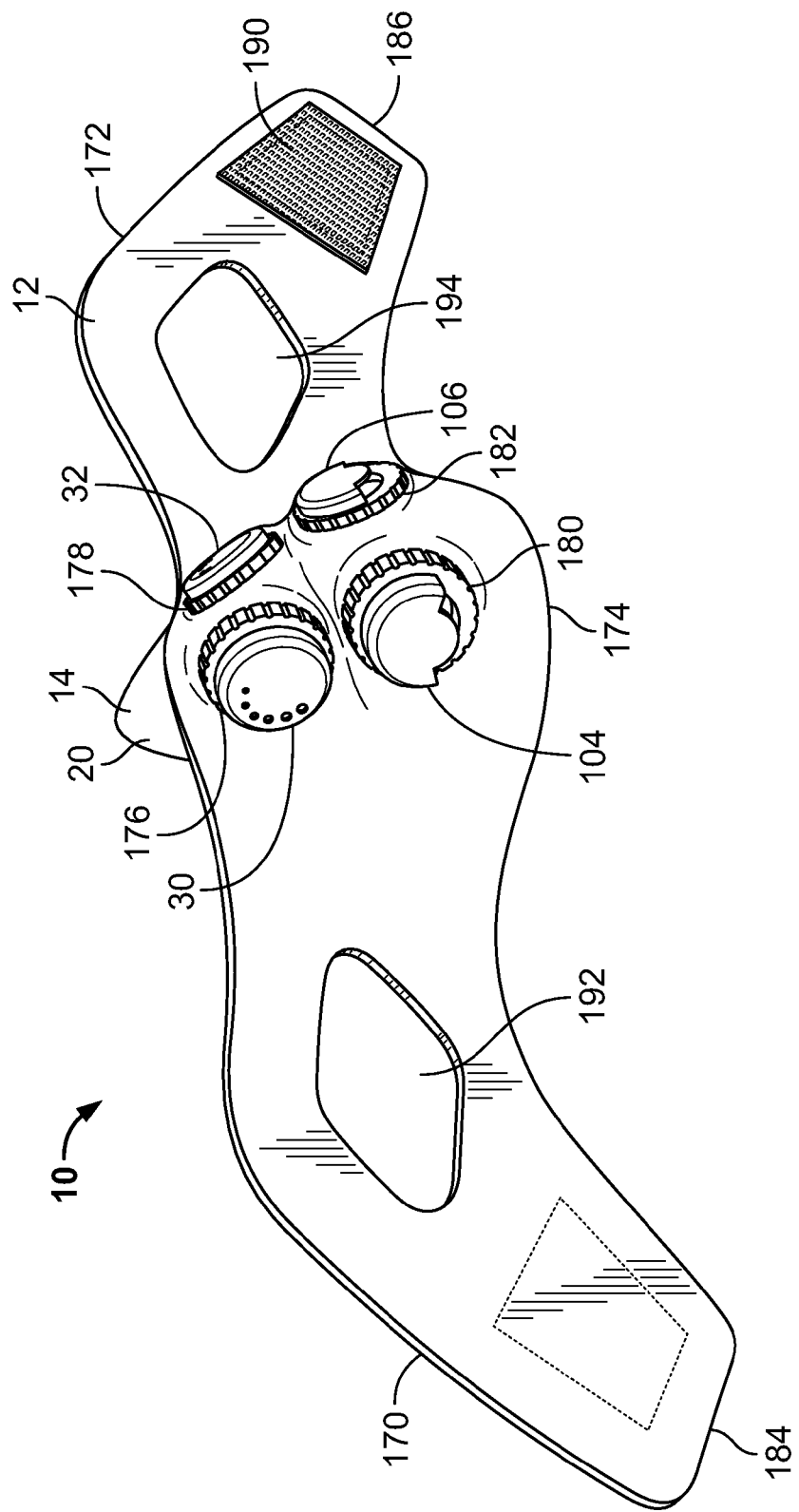
FIG. 2 is a front perspective view of the resistance breathing device shown in FIG. 1, but said device being shown as detached from the user.
Figure 3:
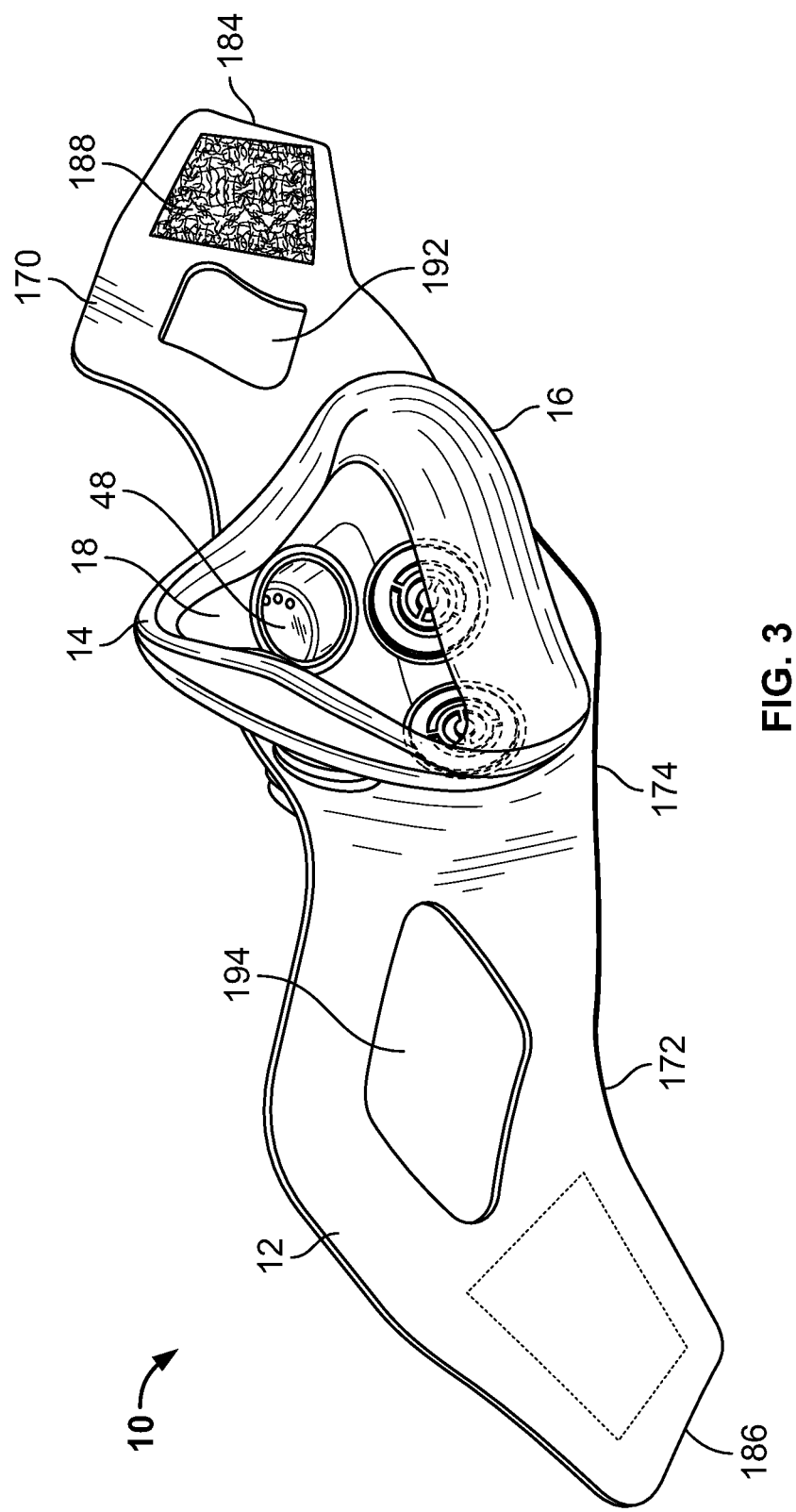
FIG. 3 is a rear perspective view of the resistance breathing device shown in FIG. 2.
Figure 4:
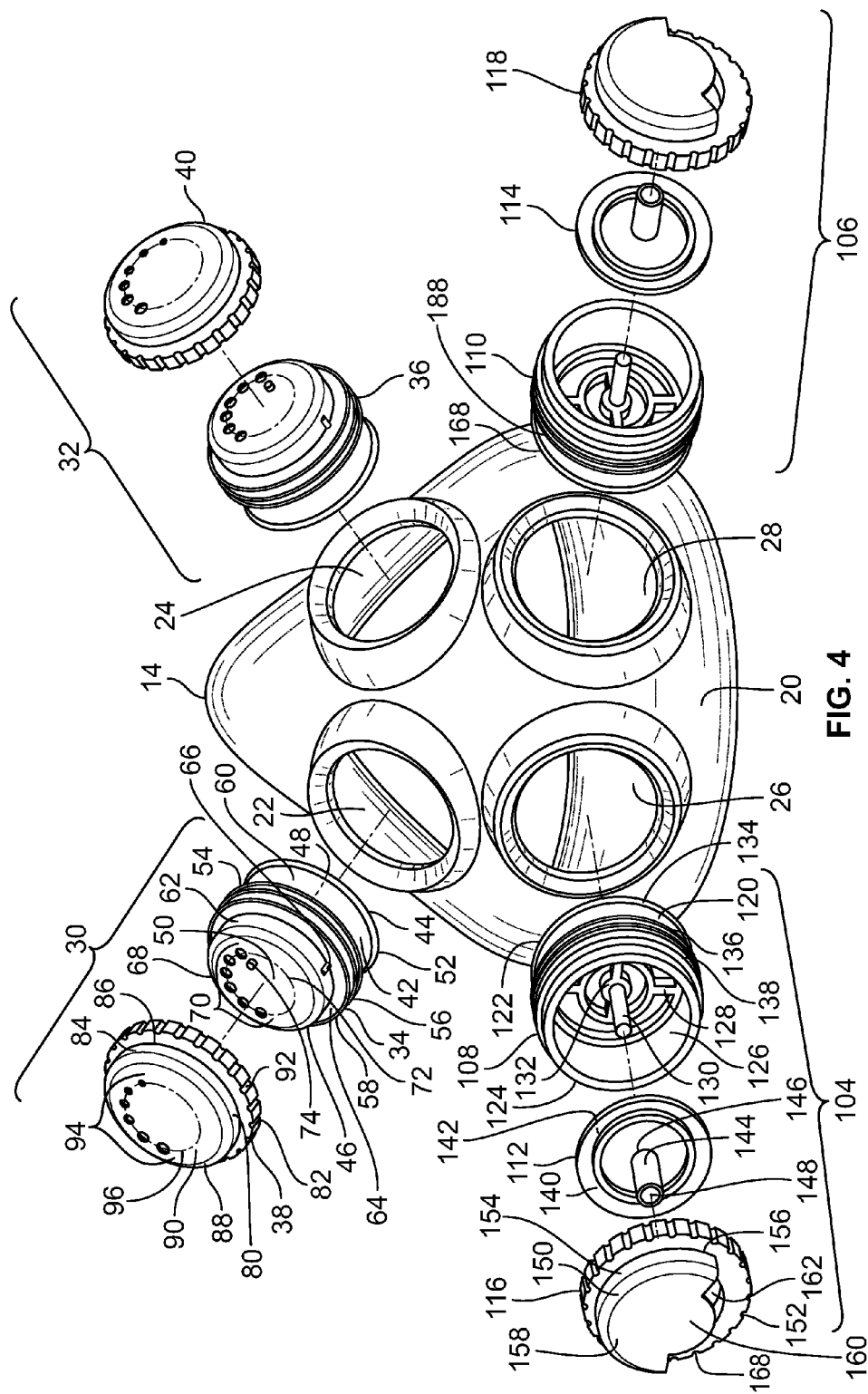
FIG. 4 is an exploded front perspective view of selected elements of the resistance breathing device shown in FIG. 2.

FIGS. 1-5 illustrate an exemplary resistance breathing device 10 (hereinafter "device 10"). In an embodiment, the device 10 includes an outer layer 12 overlaying a centrally-located, air-impermeable face mask 14. In an embodiment, the face mask 14 is sized, shaped, and adapted to overlay the nose and mouth of a user. In an embodiment, the face mask 14 includes a perimeter 16 (as shown in FIG. 3) that is adapted to provide an air-tight seal with a user's face. In an embodiment, the face mask 14 is made of an elastic material. In an embodiment, the face mask 14 is made from rubber. In another embodiment, the face mask 14 is made from other suitable materials known in the art selected such that the perimeter 16 provides an air-tight seal with a user's face. Referring now to FIGS. 2 and 3, in an embodiment, the face mask 14 includes an interior surface 18 and an exterior surface 20. Referring now to FIG. 4, in an embodiment, the face mask 14 includes apertures 22, 24, 26, 28 extending from the interior surface 18 to the exterior surface 20.

Continuing to refer to FIG. 4, in an embodiment, the device 10 includes air admittance valve assemblies 30, 32. The exemplary device 10 described herein includes two air admittance valve assemblies 30, 32, but those of skill in the art will understand that a different quantity of air admittance valve assemblies may be included in another exemplary device without departing from the broader principles delineated by the exemplary embodiments described herein. In an embodiment, each of the air admittance valve assemblies 30, 32 includes a base 34, 36 and a cap 38, 40. In an embodiment, the bases 34, 36 and the caps 38, 40 are made of a plastic material.

Continuing to refer to FIG. 4, the elements of the base 34 are now described. It will be apparent to those of skill in the art that the base 36 includes elements substantially similar to those of the base 34, but for brevity, only the base 34 will be described in detail herein. In an embodiment, the base 34 has a substantially cylindrical perimeter portion 42 having an inner end 44 and an outer end 46, and defining an air passageway 48 extending therethrough from the inner end 44 to the outer end 46. In an embodiment, the base 34 has a substantially planar end portion 50 extending across the circular cross-section of the perimeter portion 42 and obscuring the air passageway 48 at the outer end 46 of the perimeter portion 42. In an embodiment, the base 34 is open at the inner end 44 of the perimeter portion 42.

Continuing to refer to FIG. 4, in an embodiment, the base 34 has an interior retention flange 52 projecting outwardly from the perimeter portion 42 about the entire circumference thereof adjacent the inner end 44. In an embodiment, the base 34 has an exterior retention flange 54 projecting outwardly from the perimeter portion 42 about the entire circumference thereof intermediate the inner end 44 and the outer end 46. In an embodiment, the base 34 has a sealing flange 56 projecting outwardly from the perimeter portion 42 about the entire circumference thereof intermediate the exterior retention flange 54 and the outer end 46. In an embodiment, the base 34 has a cap retention flange 58 projecting outwardly from the perimeter portion 42 about the entire circumference thereof intermediate the sealing flange 56 and the outer end 46.

Continuing to refer to FIG. 4, in an embodiment, the perimeter portion 42 includes a first portion 60 extending from the inner end 44 to adjacent the cap retention flange 58. The first portion 60 has a first diameter. In an embodiment, the perimeter portion 42 also includes a second portion 62 extending from adjacent the cap retention flange 58 to the outer end 46. The second portion 62 has a second diameter that is less than the first diameter of the first portion 60. In an embodiment, the perimeter portion 42 includes a shoulder portion 64 adjacent the cap retention flange 58 providing a transition between the first portion 60 and the second portion 62. In an embodiment, the second portion 62 includes two diametrically opposed ridges 66, 68 extending radially therefrom. In an embodiment, each of the ridges 66, 62 extends longitudinally from adjacent the shoulder portion 64 toward, but not reaching, the end portion 50.

Continuing to refer to FIG. 4, in an embodiment, the base 34 includes a hole array 70. In an embodiment, each hole the hole array 70 extends through the end portion 50 of the base 34, thereby providing continuity of the air passageway 48 through the end portion 50. In an embodiment, the hole array 70 includes six holes, but those of skill in the art will understand that this is only exemplary and that varying numbers of holes may be included in the hole array 70 without departing from the broader principles of the exemplary embodiments. Because the specific quantity of holes may vary, the hole array 70 will be referred to herein collectively rather than with reference to individual holes. In an embodiment, the holes forming the hole array 70 have respective centers that are arrayed about an arc of a circle 72 that is concentric with the circular profile of the end portion 50. In an embodiment, each of the holes in the hole array 70 has the same diameter. In an embodiment, the diameters of the holes comprising the hole array 70 may vary. In an embodiment, the diameters of the holes comprising the hole array 70 may vary progressively from a largest diameter hole at a first end of the hole array to a smallest diameter hole at a second end of the hole array 70. In an embodiment, the holes forming the hole array are evenly spaced about an arc of the circle 72. In an embodiment, a cylindrical projection 74 may project from the end portion 50 proximate an end of the hole array 70 in a direction away from the inner end 44 of the base 34.

Continuing to refer to FIG. 4, the elements of the cap 38 are now described. It will be apparent to those of skill in the art that the cap 40 includes elements substantially similar to those of the cap 38, but for brevity, only the cap 38 will be described in detail herein. In an embodiment, the cap 38 includes a main portion 80 and a shoulder portion 82. In an embodiment, the main portion 80 includes a cylindrical perimeter portion 84 having a lower end 86 and an upper end 88. In an embodiment, the main portion 80 includes a planar end portion 90 extending across the circular cross-section of the perimeter portion 84 at the upper end 88 thereof. In an embodiment, the shoulder portion 82 extends from the lower end 86 of the perimeter portion 84. In an embodiment, grooves 92 are formed in the exterior of the shoulder portion 82. The grooves 92 and are sized, shaped, and positioned to enable a user of the device 10 to grip and manipulate the cap 38.

Continuing to refer to FIG. 4, in an embodiment, a hole array 94 is formed in the planar end portion 90. In an embodiment, each hole of the hole array 94 extends through the planar end portion 90 of the cap 38. In an embodiment, the hole array 94 includes the same quantity of holes as the quantity of holes in the hole array 70 of the base 34. In an embodiment, the hole array 94 includes six holes, but those of skill in the art will understand that this is only exemplary and that varying numbers of holes may be included in the hole array 94 without departing from the broader principles of the exemplary embodiments. Because the specific quantity of holes may vary, the hole array 94 will be referred to herein collectively rather than with reference to individual holes. In an embodiment, the holes forming the hole array 94 have respective centers that are arrayed about an arc of a circle 96 that is concentric with the circular profile of the planar end portion 90. In an embodiment, each of the holes in the hole array 94 has the same diameter. In an embodiment, the diameters of the holes comprising the hole array 94 may vary. In an embodiment, the diameters of the holes comprising the hole array 94 may vary progressively from a largest diameter hole at a first end of the hole array 94 to a smallest diameter hole at a second end of the hole array 94. In an embodiment, the holes forming the hole array 94 are evenly spaced about an arc of the circle 96.

Figure 5:
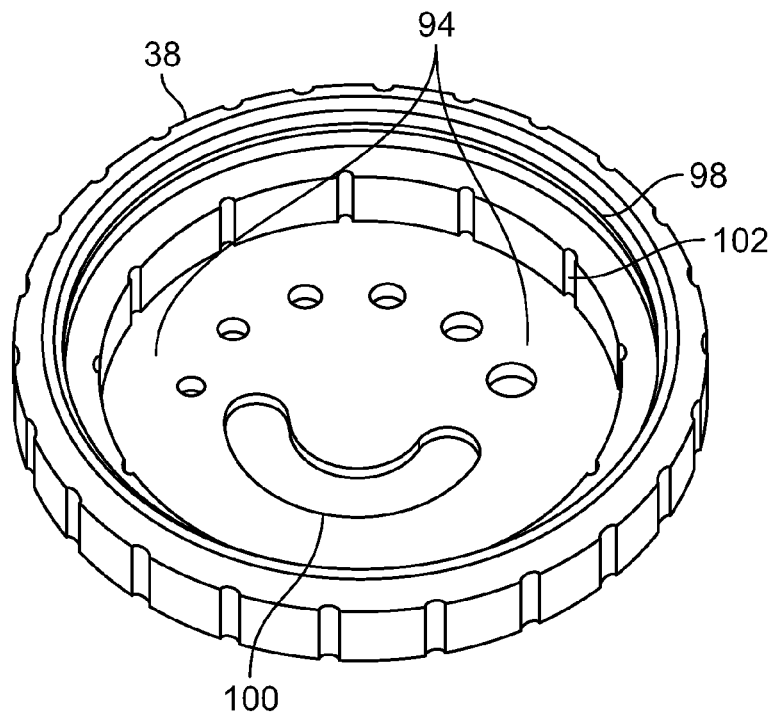
FIG. 5 is a reversed view of an element of the resistance breathing device shown in FIG. 4.

Referring now to FIG. 5, in an embodiment, a flange 98 extends from the interior of the shoulder portion 82 of the cap 38. In an embodiment, a depression 100 is formed in the inner surface of the planar end portion 90 of the cap 38. In an embodiment, the depression 100 has a curved profile and a width that is complementary to a diameter of the cylindrical projection 74 extending from the end portion 50 of the base 34. In an embodiment, a groove array 102 is formed within the inner surface of the perimeter portion 84 of the cap 38. In an embodiment, the grooves forming the groove array 102 are evenly spaced about the inner surface of the perimeter portion 84 of the cap 38. In an embodiment, the groove array 102 includes an even number of grooves, pairs of which are diametrically opposed. In an embodiment, each of the grooves of the groove array 102 is sized and shaped to receive one of the ridges 66, 68 of the base 34. In an embodiment, the quantity of grooves in the groove array 102 is twice the quantity of holes in the hole array 94; for example, in the embodiment shown in FIG. 5, the hole array 94 includes six holes, and the groove array 102 includes twelve grooves.

Referring back to FIG. 4, in an embodiment, the device 10 includes air exhaust valve assemblies 104, 106. The exemplary device 10 described herein includes two air exhaust valve assemblies 104, 106, but those of skill in the art will understand that a different quantity of air exhaust valve assemblies may be included in another exemplary device without departing from the broader principles delineated by the exemplary embodiments described herein. In an embodiment, each of the air exhaust valve assemblies 104, 106 includes a base 108, 110, a diaphragm 112, 114, and a cap 116, 118.

Continuing to refer to FIG. 4, the elements of the base 108 are now described. It will be apparent to those of skill in the art that the base 110 includes elements substantially similar to those of the base 108, but for brevity, only the base 108 will be described in detail herein. In an embodiment, the base 108 is substantially cylindrical and has a cylindrical perimeter portion 120 extending from an inner end 122 to an outer end 124 and defining an air passageway 126 extending therethrough from the inner end 122 to the outer end 124. In an embodiment, a biasing element 128 extends across the air passageway 126 proximate the inner end 122 of the perimeter portion 120. In an embodiment, a stem 130 extends from a center 132 of the biasing element 128 in a direction toward and past the outer end 124 of the perimeter portion 120. In an embodiment, an inner flange 134 extends outwardly from the perimeter portion 120 proximate the inner end 122. In an embodiment, an intermediate flange 136 extends outwardly from the perimeter portion 120 intermediate the inner end 122 and the outer end 124. In an embodiment, the inner flange 134 and the intermediate flange 136 are adapted to retain the base 108 within the aperture 22 of the face mask 14 such that the inner flange 134 abuts the interior surface 18 of the face mask 14 and the intermediate flange 136 abuts the exterior surface 20 of the face mask 14. In an embodiment, an outer flange 138 extends outwardly from the perimeter portions 120 proximate the outer end 124. In an embodiment, the bases 108, 110 are made of a plastic material.

Continuing to refer to FIG. 4, the elements of the diaphragm 112 are now described. It will be apparent to those of skill in the art that the diaphragm 114 includes elements substantially similar to those of the diaphragm 112, but for brevity, only the diaphragm 112 will be described in detail herein. In an embodiment, the diaphragm 112 has a first surface 140 and a second surface 142 opposite the first surface 140. In an embodiment, a profile of the diaphragm 112 is complementary to the air passageway 126 of the base 108. A tubular post 144 extends from the center 146 of the first surface 140. A central opening 148 extends through the diaphragm 112 from the second surface 142 and through the tubular post 144. In an embodiment, the central opening 148 sized and shaped to receive the stem 130 of the base 108 so as to enable the diaphragm 112 to be mounted within the base 108. In an embodiment, the tubular post 144 is formed integrally with the diaphragm 112 and extends generally perpendicularly from the first surface 140. In another embodiment, the tubular post 144 is a separate component from the diaphragm 112. In an embodiment, the diaphragms 112, 114 are made of silicone.

Continuing to refer to FIG. 4, the elements of the cap 116 are now described. It will be apparent to those of skill in the art that the cap 118 includes elements substantially similar to those of the cap 116, but for brevity, only the cap 116 will be described in detail herein. In an embodiment, the cap 116 includes a main portion 150 and a shoulder portion 152. In an embodiment, the main portion 150 includes a cylindrical perimeter portion 154 having a lower end 156 and an upper end 158. In an embodiment, the main portion 150 includes a planar end portion 160 extending across the circular cross-section of the perimeter portions 154 at the upper end 158. In an embodiment, the shoulder portions 152 extends from the lower end 156 of the perimeter portion 154.

Figure 6:
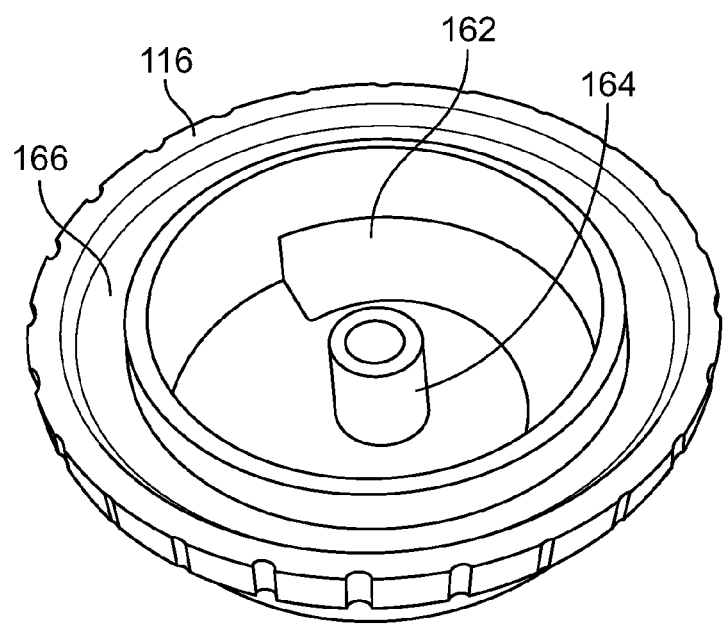
FIG. 6 is a reversed view of a further element of the resistance breathing device shown in FIG. 4.

Referring now to FIG. 6, in an embodiment, an aperture 162 passes through the main portion 150 of the cap 116. In an embodiment, the aperture 162 overlaps both the perimeter portion 154 and the planar end portion 160. In another embodiment, the cap 116 may include more than one aperture passing therethrough. In an embodiment, a post 164 extends from the planar end portion 160 of the cap 116 in a direction toward the shoulder portion 152. In an embodiment, the post 164 has a central bore that is sized, shaped and positioned to receive the stems 130 of the base 108. In an embodiment, the cap includes a groove 166 formed therein. In an embodiment, the groove 166 is sized, shaped and positioned to engage the outer end 124 and the outer flange 138 of the base 108. Referring back to FIG. 4, in an embodiment, grooves 168 are formed in the exterior of the shoulder portion 152. The grooves 168 are sized, shaped, and positioned to enable a user of the device 10 to grip and manipulate the cap 116 (e.g., to remove the cap 116 from the base 108).

Referring back to FIGS. 2 and 3, in an embodiment, the outer layer 12 includes straps 170, 172 extending in opposite directions away from a central portion 174. In an embodiment, the central portion 174 includes apertures 176, 178, 180, 182 that are sized and shaped to overlay corresponding ones of the apertures 22, 24, 26, 28. In an embodiment, the outer layer 12 is made from a fabric material. In an embodiment, the outer layer 12 is made from an elastic material. In an embodiment, the straps 170, 172 include corresponding ends 184, 186. In an embodiment, the ends 184, 186 of the straps 170, 172 incorporate corresponding hook and loop fasteners 188, 190 to enable the ends 184, 186 to be secured to one another, thereby to enable the device 10 to be affixed about the user's head (see, e.g., FIG. 1). In other embodiments, the ends 184, 186 of the straps 170, 172 include other securing means known in the art, such as clips, press-fit snaps, buttons, or the like. In an embodiment, the straps 170, 172 include cutouts 192, 194 for seating around the user's ears to further secure the device 10 to the user's face.

Referring back to FIG. 4, assembly of the device 10 will now be described. Each of the caps 38, 40 is attached to a corresponding one of the bases 34, 36 to assemble the air admittance valve assemblies 30, 32. During such attachment, the flange 98 of the cap 38 engages the cap retention flange 58 of the base 54. The sealing flange 56 of the base 34 fits flush to the shoulder portion 82 of the cap 38, preventing air from flowing therebetween. The projection 74 protruding from the end portion 50 of the base 34 engages the depression 100 formed within the cap 38.

Continuing to refer to FIG. 4, the bases 108, 110 are assembled with corresponding ones of the diaphragms 112, 114 and the caps 116, 118 to assemble the air exhaust valve assemblies 104, 106. During such attachment, the stem 130 of the base 108 is inserted into the central opening 148 of the diaphragm 112. The cap 116 is engaged to the base 108 by inserting the outer end 124 and the outer flange 138 of the base 108 into the groove 166 of the cap 116. During such insertion, the post 164 of the cap 116 receives the stem 130 of the base 108, thereby retaining the diaphragm 112 in position and assembling the air exhaust valve assembly 104.

Continuing to refer to FIG. 4, the air admittance valve assemblies 30, 32 are inserted into the face mask 14 by inserting the bases 34, 36 through the corresponding apertures 22, 24. Due to the elastic nature of the face mask 14, the apertures 22, 24 stretch to admit the corresponding bases 34, 36. When the apertures 22, 24 are allowed to return to a relaxed (i.e., not stretched) position, they form an airtight seal about the bases 34, 36, with the interior retention flange 52 of the base 34 abutting the interior surface 18 of the face mask 14 adjacent the aperture 22 and the exterior retention flanges 54 of the base 34 abutting the exterior surface 20 of the face mask 14 adjacent the aperture 22.

Continuing to refer to FIG. 4, in a similar manner, the air exhaust valve assemblies 104, 106 are inserted into the face mask 14 by inserting the bases 108, 110 through the corresponding apertures 26, 28. Due to the elastic nature of the face mask 14, the apertures 26, 28 stretch to admit the corresponding bases 108, 110. When the apertures 26, 28 are allowed to return to a relaxed (i.e., not stretched) position, they form an airtight seal about the bases 108, 110, with the inner flange 134 of the base 108 abutting the interior surface 18 of the face mask 14 adjacent the apertures 26 and the intermediate flange 136 of the base 108 abutting the exterior surface 20 of the face mask 14 adjacent the aperture 26.

Referring now to FIG. 2, the outer layer 12 is applied to the face mask 14 by stretching and pulling the apertures 176, 178, 180, 182 of the outer layer 12 over respective ones of the air admittance valve assemblies 30, 32 and the air exhaust valve assemblies 146, 148. This allows the outer layer 12 to be brought into proximity to and abut the face mask 14. When the apertures 176, 178, 180, 182 are allowed to return to a relaxed (i.e., not stretched) position, they tighten about the respective ones of the bases 34, 36, 108, 110, thereby retaining the outer layer 12 in position with respect to the bases 34, 36, 108, 110, and, thus, the face mask 14.

Referring now to FIGS. 1-7B, a method of use of the exemplary device 10 by a user will now be described. Initially, the device 10 is affixed to the user's face by placing the face mask 14 over the user's mouth and nose, passing the straps 170, 172 around either side of the user's head such that cutouts 192, 194 overlap the user's ears, and securing the ends 184, 186 to one another using the hook and loop fasteners 188, 190. The user may adjust the hook and loop fasteners 188, 190 to ensure that the face mask 14 is pulled against the user's face with sufficient force such that the perimeter 16 is pressed tightly against the user's face and around the user's mouth and nose. By such action, an airtight seal is created between the user's face and the face mask 14, thereby ensuring that air can only pass in and out for the user's inhalation and exhalation through the apertures 22, 24, 26, 28 formed within the face mask 14.

Figure 7A:
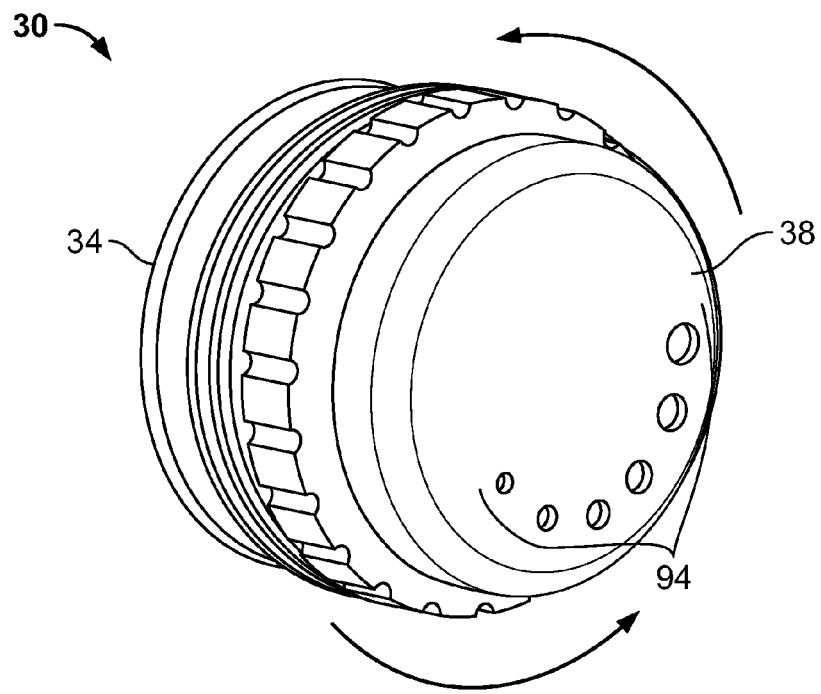
FIG. 7A is a detailed view of an assembled air admittance valve of the resistance breathing device shown in FIG. 4, showing the air admittance valve in a first configuration.
Figure 7B:
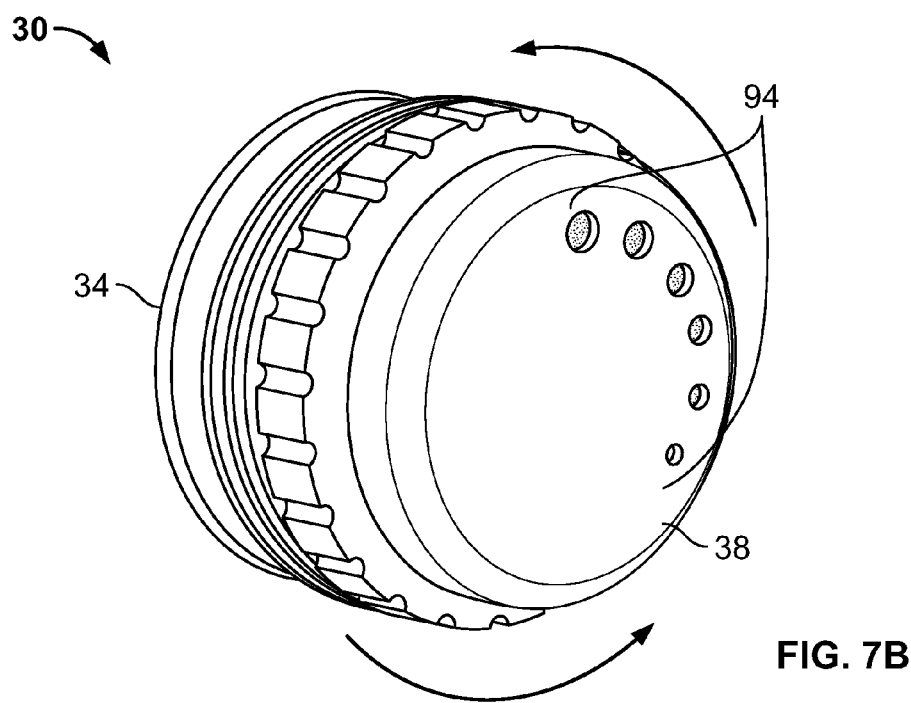
FIG. 7B is a detailed view of the assembled air admittance valve shown in FIG. 7A, but showing the air admittance valve in a second configuration.

Referring now to FIGS. 7A and 7B, the user of the device 10 may adjust the caps 38, 40 of the air admittance valve assemblies 30, 32, thereby to adjust the degree of air inhalation permitted by the device 10. What follows will be described with specific reference to the air admittance valve assembly 30, but it will be apparent to those of skill in the art that the actions described may be equally applicable to the air admittance valve assembly 32. To adjust the permitted degree of air inhalation, the user grasps the grooves 92 of the cap 38 and rotates the cap 38 with respect to the base 34; because of the tight seal formed about the base 34 by the portion of the material of the face mask 14 surrounding the aperture 22, the base 34 is retained in a static position during such rotation.

Continuing to refer to FIGS. 7A and 7B, the rotation of the cap 38 with respect to the base 34 aligns a varying number of holes of the hole array 94 of the cap 38 with those of the hole array 70 of the base 34. The cap 38 may be rotated between a position in which all of the holes of the hole array 94 of the cap 38 are aligned with corresponding ones of the holes of the hole array 70 of the base 34, as shown in FIG. 7A, and a position in which only one of the holes of the hole array 94 of the cap 38 is aligned with a corresponding one of the holes of the hole array 70 of the base 34, as shown in FIG. 7B. It will be apparent to those of skill in the art that the former position results in a maximum allowable degree of air flow through the air admittance valve assembly 30, while the latter results in a minimum allowable degree of air flow therethrough.

Continuing to refer to FIGS. 7A and 7B, the cap 38 may also positioned in various positions intermediate the position shown in FIG. 7A and that shown in FIG. 7B, which positions may provide various corresponding allowable degrees of air flow through the air admittance valve assembly 30. For example, in the embodiment of a device 10 described herein, the hole array 94 of the cap 38 and the hole array 70 of the base 34 each include six holes. Accordingly, the cap 38 may be positioned in six positions in total (i.e., the position shown in FIG. 7A, the position shown in FIG. 7B, and four positions intermediate those shown in FIGS. 7A and 7B), each of which aligns between one and six holes of the hole array 94 of the cap 38 with those of the hole array 70 of the base 34 to produce a corresponding allowable degree of air flow through the air admittance valve assembly 30.

Continuing to refer to FIGS. 7A and 7B, and also referring to FIGS. 4 and 5, the rotation of the cap 38 with respect to the base 34, as described above, is bounded by the travel of the cylindrical projection 74 of the base 34 within the depression 100 of the cap 38. The cylindrical projection 74 of the base 34 may abut a first end of the depression 100 of the cap 38 when the air admittance valve assembly 30 is positioned to allow a maximum degree of air flow therethrough, as shown in FIG. 7A, and may abut a second end of the depression 100 of the cap 38 when the air admittance valve assembly 30 is positioned to allow a minimum degree of air flow therethrough, as shown in FIG. 7B. Correspondingly, the user of the device 10 may be constrained from rotating the cap 38 in a first direction past the position where a maximum degree of air flow through air admittance valve assembly 30 is permitted (i.e., as shown in FIG. 7A), and from rotating the cap 38 in a second direction past the position where a minimum degree of air flow through air admittance valve assembly 30 is permitted (i.e., as shown in FIG. 7B).

Continuing to refer to FIGS. 4, 5, 7A and 7B, the cap 38 and the base 34 are configured to aid the user in proper alignment of the holes of the hole array 94 of the cap 38 with those of the hole array 70 of the base 34. Referring now to FIG. 4, and as previously disclosed, the base 34 includes diametrically opposed ridges 66, 68 extending from the second portion 62. Referring now to FIG. 5, and as previously disclosed, the cap 38 includes a groove array 102, grooves of which are evenly spaced about the interior surface of the perimeter portion 84, and pairs of which grooves are diametrically opposed. The holes of the hole arrays 70 and 94, the grooves of the groove array 102, and the ridges 66, 68 are arranged such that, as the cap 38 is rotated with respect to the base 34, the ridges 66, 68 are aligned with a diametrically opposed pair of grooves of the groove array 102 when one or more holes of the hole array 94 of the cap 38 are aligned with one or more holes of the hole array 70 of the base 34. Conversely, as the cap 38 is rotated with respect to the base 34, the ridges 66, 68 are not aligned with any of the diametrically opposed pairs of grooves of the groove array 102 when none of the holes of the hole array 94 of the cap 38 are aligned with holes of the hole array 70 of the base 34. It will be apparent to those of skill in the art that when the cap 38 is in such a position (i.e., when all of the holes of the hole array 94 are aligned with portions of the end portion 50 of the base 34 through which no holes extend), no air can flow through the air admittance valve assembly 30. As the user of the device 10 rotates the cap 38, the cap 38 rotates freely while the ridges 66, 68 are not arrayed with grooves of the groove array 102. Conversely, additional applied force is required to initiate rotation while the ridges 66, 68 are aligned with, and settled within, a pair of grooves of the groove array 102 because of the complementary sizing therebetween. As a result, the cap 38 may feel "settled" in place when properly aligned such that some degree of air flow through the air admittance valve assembly 30 is permitted. This tactile sensation may serve as a guide to the user of the device 10 in adjusting the air admittance valve assembly 30, particularly when the device 10 has already been fastened about the user's head and cannot readily be seen by the user.

Referring back to FIG. 4, and as previously noted, the device 10 may include a varying number of air admittance valve assemblies; for example, the device 10 described herein includes two air admittance valve assemblies 30, 32. Each of the air admittance valve assemblies 30, 32 may be configured in the manner described above with reference to FIGS. 7A and 7B and independently of one another to allow a desired degree of air flow therethrough. Therefore, the inclusion of a plurality of air admittance valve assemblies 30, 32 in the device 10 may provide the user with a variety of possible combinations. For example, in the embodiment described herein, in which the device 10 includes two air admittance valve assemblies 30, 32, each of which includes a base 34, 36 and corresponding cap 38, 40 with six holes, and each of which therefore can be placed in six different configurations (i.e., configurations in which between one and six holes are aligned to allow air to flow therethrough), the device 10 may provide thirty-six combinations of configurations for the air admittance valve assemblies 30, 32.

Continuing to refer to FIGS. 1-7B, when the user inhales, a reduced air pressure is induced within the face mask 14 as compared to the surrounding atmosphere. This reduced air pressure urges the second surface 142 of the diaphragm 112 against the biasing elements 128 of the base 108, in which position the diaphragm 112 completely overlaps and seals the air passageway 126 through the base 108. Due to such sealing, air cannot pass from the user's surroundings to within the face mask 14 through the air passageway 126 of the base 108, i.e., through the air exhaust valve assembly 104. It will be apparent to those of skill in the art that the same is true of the air exhaust valve assembly 106. As a result, the only air that can pass from the user's surroundings to within the face mask 14 is air allowed to pass through the air admittance valve assemblies 30, 32. As described above, the user of the device 10 may configure the degree of air flow allowed through the air admittance valve assemblies 30, 32 by rotating the caps 38, 40 with respect to the corresponding bases 34, 36. Therefore, by configuring the air admittance valve assemblies 30, 32, the user of the device 10 may control the amount of air that the device 10 allows him or her to inhale.

Continuing to refer to FIGS. 1-7B, when the user exhales, an increased air pressure is induced within the face mask 14 compared to the surrounding atmosphere. This increased air pressure presses outward (i.e., away from the biasing element 128) on the second surface 142 of the diaphragms 112. The diaphragms 112 prevented from moving along the stem 130 of the bases 108 due to the abutment of the post 164 of the cap 116 with the post 144 of the diaphragm 112. Thus, the increased air pressure within the face mask 14 causes the diaphragm 112 to flex outward (i.e., away from the biasing element 128), thereby opening the air passageway 126 through the base 108 for the duration of the user's exhalation and allowing exhaled air to pass from within the face mask 14 to the user's surroundings through the air exhaust valve assembly 104. It will be apparent to those of skill in the art that the same is true of the air exhaust valve assembly 106. Exhaled air may additionally pass through the air admittance valve assemblies 30, 32, though the degree of exhalation permitted therethrough is restricted in the same manner as described above with regard to inhalation.

The exemplary resistance breathing device 10 decreases the oxygen available to the body by limiting the volume of air that can be inhaled by the user during ventilation. In this regard, the device 10 simulates (i.e., as opposed to duplicating) attitude training at sea level. The user can realize benefits by having the ability to simulate a desired training stimulus without the need to travel to a training location at altitude. The user's body is unable to distinguish between a reduction in available oxygen due to an inhalation restriction and a reduction in available oxygen due to the presence of thinner air at altitude. In either case, restriction of available oxygen causes the user's body to make adaptations to adjust to the stimulus, especially if it is induced under load on a repeated basis. This adaptation results in increased serum oxygen transport to respond to the reduced oxygen state experienced during workouts.

The device 10 also exposes the user to increased carbon dioxide content during each breathing cycle. This occurs because the air that is exhaled by the user and into the device 10 cannot fully exit the device 10 before the user inhales the next breath. Carbon dioxide tolerance is an important regulator to fatigue threshold. When the respiratory center in the brain detects an elevated concentration of $CO_2$ in the blood, it sends alarm signals to the breathing musculature to cause the breathing musculature to work harder. The respiratory center also creates an undesirable sensation that causes individuals to wish to cease physical efforts. Training in this state can have significant training benefits by allowing the body to endure elevated $CO_2$ concentrations. A lack of $CO_2$ tolerance is one component (along with accumulation of lactic acid and hydrogen ions) of the physical reaction often referred to as "the wall," which causes individuals to wish to cease physical efforts. The device 10 provides the user with a means of over-inducing the physiological conditions of $CO_2$ elevation beyond what an athlete would normally experience.

Individuals may additionally have bad breathing habits, which are particularly difficult to break while training. It is possible to re-train oneself in proper diaphragmatic breathing in static positions, which can strengthen the diaphragm and produce proper breathing habits while relaxed. However, this rarely carries over into a training setting, as high stress levels can make individuals fall back into bad habits. Diaphragmatic breathing is important during training, because the diaphragm is the main element of the human breathing musculature. Other muscles, such as the intercostals and accessory muscles, are also involved in inspiration; however these muscles also share in core stabilization functions, making them prone to fatigue due to their multi-purpose role. The air resistance generated by the exemplary device 10 directly stresses the breathing musculature. This added load resets the motor program of the breathing muscles to favor a diaphragm-driven contraction sequence instead of a sequence that is dependent on accessory muscles. A diaphragm-driven contraction sequence is advantageous because a breathing cycle involving upper chest expansion coupled with rapid breaths, which can be observed in most people while breathing heavily, leads to decreased lung inflation and oxygen uptake, which ultimately decrease an individual's capacity to reduce oxygen debt during exertion.

Ideally, during labored breathing, breaths should be observed to originate in the abdomen; this indicates that an individual is using his or her diaphragm more rigorously. The exemplary device 10 helps to increase the duration of inspiration during each breathing cycle, allowing the lungs more time to expand and putting the diaphragm under load through its full muscular excursion. Repeated training with the device 10 during high intensity functional activities provides functional carryover from diaphragmatic training, which cannot be replicated simply by practicing diaphragmatic breathing in a resting position. Therefore, training with the aid of the devices 10, 210 provides a functional technique for strengthening the inspiratory musculature, which directly improves performance.

The device 10 provides a comprehensive approach for the improvement of respiratory endurance. In addition to simulating altitude training through the restriction of inhaled oxygen, the device 10 can further aid the user in improving $CO_2$ rebreathing tolerance and in improving the conditioning of respiratory muscles.

It will be understood that the embodiments described herein are merely exemplary and that a person skilled in the art may make many variations and modifications without departing from the spirit and scope of the invention. All such variations and modifications are intended to be included within the scope of the invention, as embodied in the appended claims presented.

What is claimed is:

1. A resistance breathing device, comprising:
    a face mask having an exterior surface, an interior surface opposite said exterior surface, a plurality of apertures, each of which extends through said face mask from said exterior surface to said interior surface, and a perimeter, wherein said face mask is adapted to overlay a user's mouth and nose such that said perimeter forms an air-tight seal with the user's face and around the user's mouth and nose and said face mask defines an internal area between said interior surface of said face mask and the user's face;
    an outer layer overlaying said face mask and having a pair of straps with inter-engaging ends for affixing said face mask about the user's face;

a plurality of air admittance valve assemblies, each of which is disposed within a corresponding one of said plurality of apertures of said face mask, each of said plurality of air admittance valve assemblies including a base configured to be removably fixed within said corresponding one of said plurality of apertures of said face mask and including a plurality of holes extending therethrough, each of said plurality of air admittance valve assemblies further including a cap attached to said base and including a plurality of holes extending therethrough, said cap being rotatable relative to said base between a first position, in which a first subset of holes of said plurality of holes of said cap are aligned with a corresponding first subset of holes of said plurality of holes of said base such that said base and said cap cooperate to allow a first amount of air flow through said each of said plurality of air admittance valve assemblies from an external environment to said internal area, and a second position, in which a second subset of holes of said plurality of holes of said cap are aligned with a corresponding second subset of holes of said plurality of holes of said base such that said base and said cap cooperate to allow a second amount of air flow through said each of said plurality of air admittance valve assemblies from the external environment to said internal area, said first amount of air flow being greater than said second amount of air flow, wherein said cap of each air admittance valve assembly further includes at least one groove formed therein and said base of each air admittance valve assembly includes at least one longitudinal ridge which cooperates with said at least one groove to resist rotation of said cap relative to the base; and a plurality of air exhaust valve assemblies, each of which is disposed within a corresponding one of said plurality of apertures of said face mask, each of said plurality of air exhaust valve assemblies including a base fixed within said corresponding one of said plurality of apertures of said face mask and including an air passageway extending therethrough, a flexible membrane disposed movably within said air passageway, and a cap attached to said base and retaining said flexible membrane within said air passageway wherein, in response to an inhalation by the user, said flexible membrane is urged to a first position that occludes said air passageway such that air is prevented from passing through said air passageway from the external environment to said internal area, and wherein, in response to an exhalation by the user, said flexible membrane is urged to a second position that does not occlude said air passageway such that air is enabled to pass through said air passageway from said internal area to the external environment.

2. The resistance breathing device of claim 1, wherein said base of each of said plurality of air admittance valve assemblies includes a first end, a second end opposite said first end, a cylindrical body extending from said first end to said second end, and an air passageway, said air passageway of said base of each of said plurality of air admittance valve assemblies extending through said cylindrical body of said base of each of said plurality of air admittance valve assemblies from said first end to said second end, said base of each of said plurality of air admittance valve assemblies being disposed within said corresponding one of said plurality of apertures of said face mask such that said first end of said base of each of said plurality of air admittance valve assemblies is proximate said interior surface of said face mask and said second end of said base of each of said plurality of air admittance valve assemblies is proximate said exterior surface of said face mask, said base of each of said plurality of air admittance valve assemblies being sized and shaped such that said corresponding one of said plurality of apertures of said face mask forms an air-tight seal about said base of each of said plurality of air admittance valve assemblies.

3. The resistance breathing device of claim 2, wherein said base of each of said plurality of air admittance valve assemblies includes an end portion occluding said air passageway of said base proximate said second end of said base, said plurality of holes of said base of each of said plurality of air admittance valve assemblies extending through said end portion, said plurality of holes of said base of each of said plurality of air admittance valve assemblies being arranged in arcuate arrangement,
wherein said plurality of holes of said cap of each of said plurality of said air admittance valve assemblies is arranged in arcuate arrangement.

4. The resistance breathing device of claim 3, wherein said base of each of said plurality of air admittance valve assemblies includes a projection extending from said end portion of said base toward said cap of said each of said plurality of air admittance valve assemblies, wherein said cap of said each of said plurality of air admittance valve assemblies includes a depression receiving said projection of said base of said each of said plurality of air admittance valve assemblies therein, said depression having a first end and a second end opposite said first end, and wherein the rotation of said cap of said each of said plurality of air admittance valve assemblies relative to said base of said each of said plurality of air admittance valve assemblies causes said depression of said cap of said each of said plurality of air admittance valve assemblies to move relative to said projection of said base of said each of said plurality of air admittance valve assemblies such that said first end of said depression of said cap of said each of said plurality of air admittance valve assemblies is adjacent said projection of said base of said each of said plurality of air admittance valve assemblies when one of said plurality of holes of said cap of said each of said plurality of air admittance valve assemblies is aligned with one of said plurality of holes of said base of said each of said plurality of air admittance valve assemblies, and such that said second end of said depression of said cap of said each of said plurality of air admittance valve assemblies is adjacent said projection of said base of said each of said plurality of air admittance valve assemblies when each of said plurality of holes of said cap of said each of said plurality of air admittance valve assemblies is aligned with a corresponding one of said plurality of holes of said base of said each of said plurality of air admittance valve assemblies.

5. The resistance breathing device of claim 3, wherein said at least one longitudinal ridge of said base of each of said plurality of air admittance valve assemblies and said at least one groove of said cap of said each of said plurality of air admittance valve assemblies are positioned such that said at least one longitudinal ridge is positioned within a corresponding one of said at least one groove when one or more of said plurality of holes of said cap of said each of said plurality of air admittance valve assemblies is aligned with a corresponding one of said plurality of holes of said base of said each of said plurality of air admittance valve assemblies.

6. The resistance breathing device of claim 2, wherein said base of each of said plurality of air admittance valve assemblies comprises at least one flange sized, shaped and positioned to retain said base within said face mask.

7. The resistance breathing device of claim 2, wherein said base of each of said plurality of air admittance valve assemblies and said cap of each of said plurality of air admittance valve assemblies are each made from a plastic material.

8. The resistance breathing device of claim 1, wherein said base of each of said plurality of air exhaust valve assemblies includes a first end and a second end opposite said first end, said air passageway of said base of each of said plurality of air exhaust valve assemblies extending therethrough from said first end to said second end, said base of each of said plurality of air exhaust valve assemblies being disposed within said corresponding one of said plurality of apertures of said face mask such that said first end of said base of each of said plurality of air exhaust valve assemblies is proximate said interior surface of said face mask and said second end of said base of each of said plurality of air exhaust valve assemblies is proximate said exterior surface of said face mask, said base of each of said plurality of air exhaust valve assemblies being sized and shaped such that said corresponding one of said plurality of apertures of said face mask forms an air-tight seal about said base of said each of said plurality of air exhaust valve assemblies, said base of each of said plurality of air exhaust valve assemblies further including a biasing member extending across said air passageway proximate said first end, and a stem extending from a center of said biasing member toward said second end, wherein said flexible membrane of each of said plurality of air exhaust valve assemblies includes a first side, a second side opposite said first side, a profile complementary to said air passageway of said base of said each of said plurality of air exhaust valve assemblies, a post extending from said first side, and a central hole extending through said post and said flexible membrane, said flexible membrane of each of said plurality of air exhaust valve assemblies being disposed within said base of said each of said plurality of air exhaust valve assemblies such that said stem of said base of said each of said plurality of air exhaust valve assemblies is disposed within said central hole of said flexible membrane of said each of said plurality of air exhaust valve assemblies, and wherein said cap of each of said plurality of air exhaust valve assemblies includes a first side and a second side opposite said first side of said cap, said cap of each of said plurality of air exhaust valve assemblies being attached to said second end of said base of said each of said plurality of air exhaust valve assemblies, said cap of each of said plurality of air exhaust valve assemblies having a post extending from said first side of said cap and having a central bore receiving said stem of said base of said each of said plurality of air exhaust valve assemblies.

9. The resistance breathing device of claim 8, wherein, in response to the inhalation by the user, said flexible membrane of each of said air exhaust valve assemblies is urged to a position flush against said biasing member of said base of said each of said plurality of air exhaust valve assemblies, whereby said flexible membrane of each of said plurality of air exhaust valve assemblies seals said air passageway of said base of said each of said plurality of air exhaust valve assemblies.

10. The resistance breathing device of claim 8, wherein, in response to the exhalation by the user, said flexible membrane of each of said air exhaust valve assemblies is urged away from said biasing member of said base of said each of said air exhaust valve assemblies, whereby air can pass freely through said air passageway of said base of each of said air exhaust valve assemblies.

11. The resistance breathing device of claim 8, wherein said flexible membrane of each of said air exhaust valve assemblies is made from silicone.

12. The resistance breathing device of claim 8, wherein said cap of each of said air exhaust valve assemblies and said base of each of said air exhaust valve assemblies are each made from a plastic material.

13. The resistance breathing device of claim 8, wherein said base of each of said air exhaust valve assemblies includes at least one flange sized, shaped and positioned to retain said base within said face mask.

14. The resistance breathing device of claim 1, wherein said outer layer includes a fabric material.

15. The resistance breathing device of claim 14, wherein said fabric material includes an elastic material.

16. The resistance breathing device of claim 1, wherein said straps of said outer layer include hook-and-loop fasteners.

17. The resistance breathing device of claim 1, wherein said face mask includes rubber.

* * * * *